(12) United States Patent
Weintritt et al.

(10) Patent No.: US 6,255,486 B1
(45) Date of Patent: Jul. 3, 2001

(54) PROCESS FOR PREPARING 4,6-DICHLORO-5-FLUOROPYRIMIDINE

(75) Inventors: Holger Weintritt, Langenfeld; Reinhard Lantzsch, Wuppertal, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/641,271

(22) Filed: Aug. 17, 2000

(30) Foreign Application Priority Data

Aug. 18, 1999 (DE) ............... 199 39 190
Oct. 11, 1999 (DE) ............... 199 48 933

(51) Int. Cl.[7] ............... C07D 239/30
(52) U.S. Cl. ............... 544/334
(58) Field of Search ............... 544/334

(56) References Cited

U.S. PATENT DOCUMENTS

| 3,694,444 | 9/1972 | Klauke et al. | 260/251 R |
| 5,391,811 | 2/1995 | Böhm et al. | 560/43 |
| 5,523,404 | 6/1996 | Zurmühlen | 544/319 |
| 5,677,453 | 10/1997 | Cramm et al. | 544/334 |
| 5,847,139 | 12/1998 | Hunds | 544/319 |

FOREIGN PATENT DOCUMENTS

| 196 42 533 | 4/1998 | (DE) . |
| 61-205262 | 11/1986 | (JP) . |
| 97/44327 | 11/1997 | (WO) . |
| 98/41513 | 9/1998 | (WO) . |

Primary Examiner—John M. Ford
(74) Attorney, Agent, or Firm—Joseph C. Gil

(57) ABSTRACT

The invention relates to a novel process for preparing 4,6-dichloro-5-fluoropyrimidine.

8 Claims, No Drawings

PROCESS FOR PREPARING 4,6-DICHLORO-5-FLUOROPYRIMIDINE

This application claims priority to German Applications 19939190.4 and 19948933.5 filed on Aug. 18, 1999 and Oct. 11, 1999 respectively.

The invention relates to a novel process for preparing 4,6-dichloro-5-fluoropyrimidine.

BACKGROUND OF THE INVENTION 4,6-dichloro-5-fluoropyrimidine is an intermediate which can be used, for example, for preparing crop protection agents and dyes.

A process for preparing 4,6-dichloro-5-fluoropyrimidine has already been described In DE-A1-197 10609.

In this process, 4,6-dihydroxy-5-fluoropyrimidine is admixed with phosphorus oxychloride and dimethylaniline as base. For work-up, firstly the excess phosphorus oxychloride is distilled off and the residue is subjected to vacuum distillation. This process has the disadvantage that a relatively large amount of base is employed, and that the base can be recovered and re-used only at great cost. Moreover, during the aqueous work-up of the distillation residue, large amounts of wastewater with a high phosphate content are formed. Work-up on an industrial scale is therefore very complicated.

The preparation of 4,6-dichloropyrimidine is described in DE-A1-196 42 533 and DE-A1-195 31 299.

A process for preparing 4,6-dihydroxy-5-fluoropyrimidine is described in JP-A2-61 205 262. In this process, the condensing agent used is formamide hydrochloride, which is a relatively expensive and highly hygroscopic condensing agent. Accordingly, this process is no alternative for industrial production.

Processes for preparing 4,6-dihydroxypyrimidine derivatives have likewise already been described (cf. WO-A1-94/44327, DE-A1-43 23 180, U.S. Pat. No. 847 139).

BRIEF SUMMARY OF THE INVENTION

Accordingly, it was the object of the present invention to provide a process for preparing 4,6-dichloro-5-fluoropyrimidine which allows the preparation on an industrial scale without addition of bases and where phosphate-containing wastes are avoided or produced in only small amounts.

DETAILED DESCRIPTION OF THE INVENTION

It has now been found that 4,6-dichloro-5-fluoropyrimidine (I)

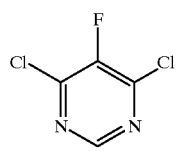

(I)

is obtained when a) compounds of the formula (II),

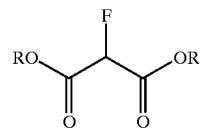

(II)

in which
R represents methyl or ethyl are reacted with formamide in the presence of alkali metal alkoxides, if appropriate in a diluent at elevated temperature, if appropriate under pressure, and the reaction mixture is, if appropriate, acidified with an acid after the reaction, and, if appropriate without intermediate isolation of the compounds of the formula (III), b) the resulting 4,6-dihydroxy-5-fluoropyrimidine (III) or its alkali metal salt

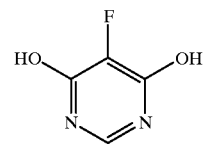

(III)

is reacted with phosphorus oxychloride, and the resulting reaction mixture 1 is subsequently reacted with chlorine in the presence of phosphorus trichloride such that in each case at most 99.9% by weight of the chlorophosphonic acids which are present in the reaction mixture are converted, and the resulting reaction mixture 2 is worked up distillatively, whereby the 4,6-dichloro-5-fluoropyrimidine formed is separated off and the phosphorus oxychloride is recovered.

In a particularly preferred variant, the compounds of the formula (II) are added, if appropriate in a diluent, to a mixture of formamide, alkali metal alkoxides and diluent.

The process according to the invention has the advantages that the condensing agent used in process step a) is formamide.

A further advantage of the novel process is the fact that the chlorination according to process step b) can be carried out without bases. Moreover, the formation of large amounts of phosphate-containing wastewater is avoided, and the phosphorus oxychloride can be recovered.

The process according to the invention for preparing 4,6-dichloro-5-fluoropyrimidine is therefore more environmentally friendly than the processes known to date.

The starting materials of the formula (II) are known substances and can be prepared by simple processes (cf. DE 42 57 882).

All other starting materials are likewise customary commercial products, or they can be prepared from these by simple processes.

In the formula (II), R represents in particular ethyl.

Suitable diluents for carrying out the process step a) are, by way of example and by way of preference, alcohols, in particular alcohols having 1 to 4 carbon atoms, especially methanol.

The preferred diluent for carrying out the process step b) is an excess of phosphorus oxychloride.

For the purpose of the invention, alkali metal alkoxides are potassium alkoxides and in particular sodium alkoxides which are derived from alcohols having 1 to 4 carbon atoms.

For the purpose of the invention, acids are relatively highly concentrated acids, in particular mineral acids, by way of example and by way of preference sulphuric acid, phosphoric acid and in particular hydrochloric acid.

When carrying out the process according to the invention, the reaction temperatures can be varied within a relatively wide range. In general, the process is carried out in a temperature range from 50° C. to the reflux temperature of the mixture in question, in particular at reflux temperature.

The reaction of compounds of the formula (II) according to process step a) is carried out at atmospheric pressure in a temperature range from 50° C. to reflux temperature, preferably in a temperature range from 60° C. to reflux temperature, and under superatmospheric pressure in a temperature range from 60° C. to 120° C., preferably in a temperature range from 80° C. to 110° C.

The reaction of compounds of the formula (III) according to process step b) is preferably carried out in a temperature range from 60° C. to reflux temperature, in particular at from 80° C. to reflux temperature.

The reactions of the process according to the invention are carried out under atmospheric pressure, under elevated or under reduced pressure, preferably under atmospheric pressure.

The reaction of compounds of the formula (II) according to process step a) is carried out under atmospheric pressure or under elevated pressure, in particular under pressures of from 1 to 4 bar, preferably under pressures of from 1.5 to 3 bar.

The reaction of compounds of the formula (III) according to process step b) is preferably carried out under atmospheric pressure.

For carrying out the process according to the invention for preparing the compounds of the formula (III), in process step a), in general from 2 to 10 mol, preferably from 2.5 to 8 mol, of formamide and from 3 to 6 mol, preferably from 3 to 4 mol, of alkali metal alkoxide are employed per mole of the compound of the formula (II).

For carrying out the process according to the invention for preparing the compounds of the formula (I), in process step b), in general from 2.5 to 12 mol, preferably from 3 to 8 mol, of phosphorus oxychloride are employed per mole of the compound of the formula (III).

For carrying out the process according to the invention for preparing compounds of the formula (I), in process step b), in general from 1.7 to 2.1 equivalents, preferably from 1.9 to 2.0 equivalents, of chlorine are employed per mole of the compounds of the formula (III).

For carrying out the process according to the invention for preparing the compounds of the formula (I), in process step b), in general from 1.7 to 2.1 equivalents, preferably from 1.9 to 2.0 equivalents, of phosphorus trichloride are employed per mole of the compounds of the formula (III).

The addition of compounds of the formula (II) according to process step a) or of a mixture of compounds of the formula (II) and formamide is, in particular, carried out by dropwise addition of compounds of the formula (II) which are, if appropriate, dissolved in an alcohol having 1 to 4 carbon atoms, or of a mixture of compounds of the formula (II) and formamide which is, if appropriate, dissolved in an alcohol having 1 to 4 carbon atoms, at temperatures of from 50° C. to reflux temperature, in particular at reflux temperature.

It is a feature of the invention that the addition of the fluoromalonic ester in process step a) is carried out by continuous metered addition of a solution of the fluoromalonic ester, if appropriate in an alcohol having 1 to 4 carbon atoms, to the reaction mixture which is present. Particular preference is given to processes in which the addition is carried out by slow metered addition, in particular over a period of from 1 to 10 hours, preferably over a period of from 2 to 4 hours.

In process step b), after the reaction of 4,6-dihydroxy-5-fluoropyrimidine with phosphorus oxychloride has taken place, phosphorus trichloride and the amount of chlorine stated above are added to the reaction mixture such that in each case at most 99.9% by weight of the chlorophosphonic acid which is present in the reaction mixture are converted. Preference is given here to initially adding phosphorus trichloride and then adding chlorine.

The addition of phosphorus trichloride and chlorine is carried out at temperatures of from 80° C. to reflux temperature, preferably at reflux temperature.

The practice of the reaction and the work-up and isolation of the reaction products are carried out by generally customary processes (compare also the Preparation Examples).

The process according to the invention is used for preparing 4,6-dichloro-5-fluoropyrimidine (I) which is an important intermediate for preparing pesticides. By the process according to the invention, it is possible to obtain 4,6-dichloro-5-fluoropyrimidine in constantly high purities and good yields. Accordingly, the novel process facilitates the preparation of known pesticides.

The examples below serve to illustrate the invention. However, the invention is not limited to the examples.

PREPARATION EXAMPLES

Example 1

4,6-Dihydroxy-5-fluoropyrimidine

30% sodium methoxide in methanol (18.9 g, 0.105 mol) are rapidly admixed with formamide (4.7 g, 0.105 mol), and the mixture is heated to reflux temperature. At reflux, ethyl fluoromalonate (5.3 g, 28.5 mmol, content: 95%) dissolved in methanol (30 ml) is then added dropwise over a period of 3 h, and the mixture is stirred at reflux temperature for another 18 h. The suspension is concentrated completely under reduced pressure, the residue is dissolved in water (10 ml) and the pH of the solution is adjusted to pH 1 using 30% HCl. The resulting precipitate is then filtered off with suction and dried under reduced pressure at 100° C. overnight. This gives 4,6-dihydroxy-5-fluoropyrimidine (3.06 g, content (HPLC-STD): 74.2%; 61.4% of theory) as a solid.

Example 2

4,6-Dihydroxy-5-fluoropyrimidine

30% sodium methoxide in methanol (18.9 g, 0.105 mol) are rapidly admixed with formamide (4.7 g, 0.105 mol), and the mixture is heated to reflux temperature. At reflux, ethyl fluoromalonate (5.3 g, 28.5 mmol, content: 95%) dissolved in methanol (10 ml) is then added dropwise over a period of 3 h, and the reaction mixture is transferred with methanol (20 ml) into an autoclave and stirred at 100° C. for another 3 h (about 2.5 to 3 bar). The suspension is concentrated completely under reduced pressure, the residue is dissolved in water (10 ml) and the pH of the solution is adjusted to pH 1 using 30% HCl. The resulting precipitate is then filtered off with suction and dried under reduced pressure at 100° C. overnight. This gives 4,6-dihydroxy-5-fluoropyrimidine (3.01 g, content (HPLC-STD): 79.3%; 64.4% of theory) as a solid.

Example 3

4,6-Dihydroxy-5-fluoropyrimidine

30% sodium methoxide in methanol (63.0 g, 0.35 mol) are rapidly admixed with formamide (22.5 g, 0.5 mol) and the mixture is heated to reflux temperature. At reflux, ethyl fluoromalonate (17.8 g, 95.0 mmol, content: about 95%) is then added over a period of 225 min, and the mixture is stirred at reflux temperature for a further 3 h. The suspension is concentrated completely under reduced pressure, the residue is dissolved in water (65 ml) and the pH of the solution is adjusted to pH 1 using 30% HCl. The resulting precipitate is then filtered off with suction and dried at 100° C. under reduced pressure overnight. This gives 4,6-dihydroxy-5-fluoropyrimidine (11.74 g, content (HPLC-STD): 82.5%; 78.4% of theory) as a solid.

Example 4

4,6-Dihydroxy-5-fluoropyrimidine

30% sodium methoxide in methanol (63.0 g, 0.35 mol) are rapidly admixed with formamide (33.75 g, 0.75 mol) and the mixture is heated to reflux temperature. At reflux, ethyl fluoromalonate (17.8 g, 95.0 mmol, content: about 95%) is then added over a period of 200 min, and the mixture is stirred at reflux temperature for a further 3 h. The suspension is concentrated completely under reduced pressure, the residue is dissolved in water (65 ml) and the pH of the solution is adjusted to pH 1 using 30% HCl. The resulting precipitate is then filtered off with suction and dried at 100° C. under reduced pressure overnight. This gives 4,6-dihydroxy-5-fluoropyrimidine (12.1 g, content (HPLC-STD): 90.2%; 88.3% of theory) as a solid.

Example 5

4,6-Dichloro-5-fluorpyrimidine 51.8 g (0.375 mol, content: 94.2%) of 4,6-dihydroxy-5-fluoropyrimidine are suspended in 287.4 g (1.875 mol) of POCl$_3$, and the mixture is heated to reflux temperature and stirred at this temperature for 4 hours. Under reflux, 102 g (0.74 mol) of phosphorus trichloride are then added to the reaction mixture, 52.6 g (0.74 mol) of Cl$_2$ are then introduced and stirring is continued at reflux temperature for 4 h. After the reaction has ended, phosphorus oxychloride together with the product is separated off under reduced pressure from the residue (8.9 g), and the resulting distillate (445.6 g) is subjected to fine distillation. This gives 384.3 g of POCl$_3$ (95.8% of theory, content: >99.5%) and 52.5 g of 4,6-dichloro-5-fluoropyrimidine (81.6% of theory, content: 97.3%) as colourless liquids.

What is claimed is:
1. A process for preparing 4,6-dichloro-5-fluoropyrimidine (I),

comprising
a) reacting a compound of the formula (II),

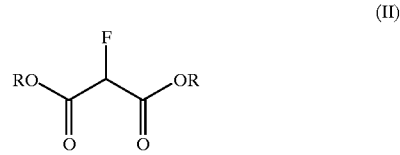

in which
R represents methyl or ethyl with formamide in the presence of alkali metal alkoxides, optionally in a diluent at elevated temperature, optionally, under pressure, and the reaction mixture is, optionally acidified with an acid after the reaction, and, optionally without intermediate isolation of the compounds of the formula (III),
b) reacting the resulting 4,6-dihydroxy-5-fluoropyrimidine (III) or its alkali metal salt

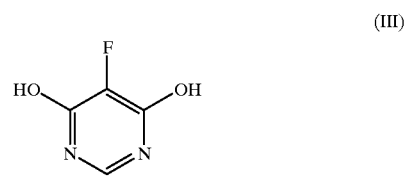

with phosphorus oxychloride, to form reaction mixture 1, subsequently reacting reaction mixture 1 with chlorine in the presence of phosphorus trichloride such that up to 99.9% by weight of any chlorophosphonic acid is converted to phosphorous oxychloride, thereby forming reaction mixture 2, and distilling reaction mixture 2 to separate the 4,6-dichloro-5-fluoropyrimidine formed and to recover the phosphorus oxychloride.

2. The process according to claim 1 wherein, in process step a) for preparing the compound of formula (III), 2 to 10 mol of formamide and 3 to 6 mol of alkali metal alkoxide are employed per mole of the compound of the formula (II).

3. The process of claim 1, further comprising adding the compound of formula (II) to a mixture of formamide and alkali metal alkoxide, optionally in a diluent.

4. The process of claim 1, further comprising reacting in process step b) 2.5 to 12 mol of phosphorus oxychloride per mole of the compound of the formula (III).

5. The process of claim 1, further comprising reacting in process step b) 1.7 to 2.1 equivalents of chlorine per mole of the compound of formula (III).

6. The process of claim 1, further comprising reacting in process step b) 1.7 to 2.1 equivalents of phosphorus trichloride per mole of the compound of the formula (III).

7. The process of claim 1, wherein in process step a), compounds of the formula (II) are added by slow metered addition.

8. The process of claim 1, wherein the process is carried out as a one-pot process.

* * * * *